United States Patent [19]

Ando et al.

[11] Patent Number: 5,287,059
[45] Date of Patent: Feb. 15, 1994

[54] SATURABLE CORE MAGNETOMETER WITH A PARALLEL RESONANT CIRCUIT IN WHICH THE W3 DC LEVEL CHANGES WITH A CHANGE IN AN EXTERNAL MAGNETIC FIELD

[75] Inventors: Seigo Ando, Tokyo; Yoshihiro Murakami, Mitaka, both of Japan

[73] Assignee: NKK Corporation, Tokyo, Japan

[21] Appl. No.: 807,863

[22] PCT Filed: Apr. 25, 1991

[86] PCT No.: PCT/JP91/00561
§ 371 Date: Jan. 14, 1992
§ 102(e) Date: Jan. 14, 1992

[87] PCT Pub. No.: WO91/18299
PCT Pub. Date: Nov. 28, 1991

[30] Foreign Application Priority Data

May 19, 1990 [JP] Japan .................................. 2-128119
Oct. 19, 1990 [JP] Japan .................................. 2-278918

[51] Int. Cl.⁵ ...................... G01R 33/04; G01C 17/28
[52] U.S. Cl. ...................................... 324/253; 324/260
[58] Field of Search ............... 322/244, 253, 254, 255; 324/256, 258, 260; 33/361

[56] References Cited

U.S. PATENT DOCUMENTS 4,503,395  3/1985  Kratzer et al. ...................... 324/253

FOREIGN PATENT DOCUMENTS

51-15481  2/1976  Japan .
52-39307  10/1977  Japan .
58-21172  2/1983  Japan .
60-57275  4/1985  Japan .
1-235213  9/1989  Japan .
1-308982  12/1989  Japan .

Primary Examiner—Walter E. Snow
Attorney, Agent, or Firm—Frishauf, Holtz, Goodman & Woodward

[57] ABSTRACT

A magnetism detecting apparatus of this invention includes a magnetic sensor (11) constituted by a ferromagnetic core (12) and a detection coil (13) wound around the core (12), a parallel resonance circuit (15) constituted by the detection coil (13) of the magnetic sensor (11) and a capacitance element (14) connected in parallel with the detection coil (13), an oscillation circuit (18), which is constituted by an amplifier (16) to which the parallel resonance circuit (15) and a resistor (17) are connected as a feedback circuit, and the parallel resonance circuit (15), and excites the core (12) to a saturation region by using an oscillation current, and a waveform change detecting circuit (22, 24) for detecting a change in waveform of an output signal from the oscillation circuit (18). That is, the core (12) is excited to the saturation region by the oscillation circuit (18) using the detection coil (13) of the magnetic sensor (11) as part of the parallel resonance circuit (15), and an external magnetic field (H) applied to the magnetic sensor (11) is detected on the basis of the amount of change in waveform of an output signal (a) from the oscillation circuit (18). As a result, the circuit arrangement can be simplified, and a reduction in size and manufacturing cost of the overall apparatus can be realized while maintaining high measurement precision.

4 Claims, 6 Drawing Sheets

SATURABLE CORE MAGNETOMETER WITH A PARALLEL RESONANT CIRCUIT IN WHICH THE W3 DC LEVEL CHANGES WITH A CHANGE IN AN EXTERNAL MAGNETIC FIELD

TECHNICAL FIELD

The present invention relates to a magnetism detecting apparatus incorporating a saturable type magnetic sensor and, more particularly, to a magnetism detecting apparatus in which a detection coil wound around a core is incorporated, as a resonance circuit, in an oscillation circuit so that the oscillation circuit acquires both an excitation function of exciting a magnetic sensor and a detection function of extracting a detection signal from the magnetic sensor.

BACKGROUND ART

A magnetism detecting apparatus incorporating a saturable type magnetic sensor can detect magnetism with high precision (Published Unexamined Japanese Patent Application No. 1-308982).

Figure 5:
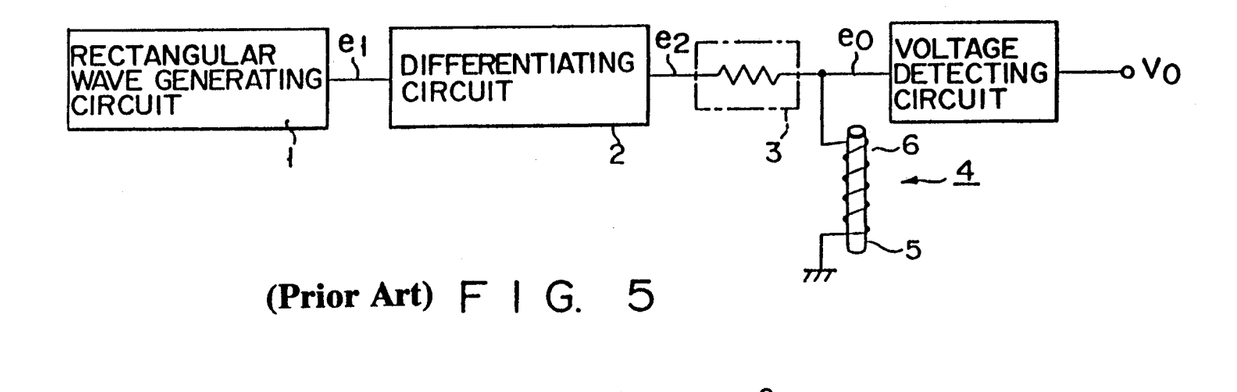
FIG. 5 is a block diagram showing a schematic arrangement of a conventional magnetism detecting apparatus.
Figure 6:
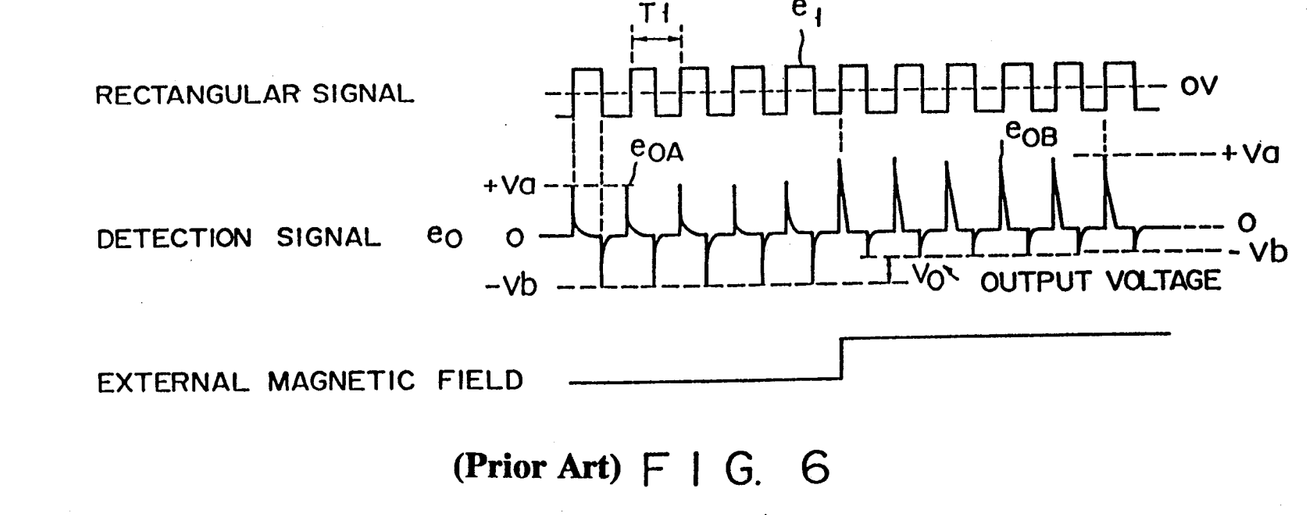
FIG. 6 is a timing chart showing an operation of the conventional apparatus.

FIG. 5 is a block diagram showing a schematic arrangement of a magnetism detecting apparatus using a saturable type magnetic sensor. A rectangular wave generating circuit 1 outputs an AC rectangular signal $e_1$ having a predetermined period $T_1$, as shown in FIG. 6. A 0-volt line is located in the middle of the signal waveform of the rectangular signal $e_1$. The rectangular signal $e_1$ output from the rectangular wave generating circuit 1 is input to a differentiating circuit 2. The differentiating circuit 2 differentiates the rectangular signal $e_1$. As a result, the differentiating circuit 2 outputs a pulse signal having a trigger waveform, which is synchronized with the leading and trailing edges of a rectangular wave included in the rectangular signal $e_1$.

The pulse having the trigger waveform, output from the differentiating circuit 2, is applied, as an AC excitation signal $e_2$, to a magnetic sensor 4 through an impedance element 3 constituted by a resistor. This magnetic sensor 4 is constituted by a rod-like ferromagnetic core 5 and a detection coil 6 wound around the core 5. The AC excitation signal $e_2$ is applied to one end of the detection coil 6 of the magnetic sensor 4 through the impedance element 3. The other end of the detection coil 6 is grounded. The terminal voltage of the detection coil 6 is extracted as a detection signal $e_0$ obtained by the magnetic sensor 4 and is input to a voltage detecting circuit 7.

The voltage detecting circuit 7 comprises a positive detector for detecting a positive peak voltage $+Va$ of the detection signal $e_0$ shown in FIG. 6, a negative detector for detecting a negative peak voltage $-Vb$ of the detection signal $e_0$, and an adder for adding the peak voltages $+Va$ and $-Vb$ detected by the respective detectors. An output voltage $V_0$ corresponding to a magnetic field strength detected by the magnetism detecting apparatus is obtained by the voltage detecting circuit 7.

An operation principle of the magnetic sensor 4 will be described below with reference to FIGS. 7 to 11.

Figure 7:
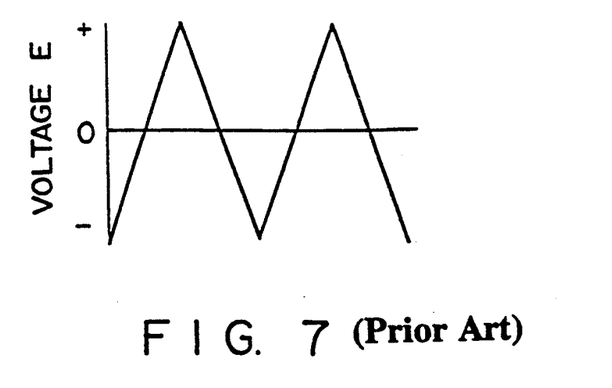
FIG. 7 is a graph showing the waveform of a voltage to be applied to a detection coil of a magnetic sensor.

AC power having an AC voltage waveform shown in FIG. 7 is applied to the detection coil 6 of the magnetic sensor 4 through the resistor of the impedance element 3. In this case, a voltage $e0$ generated across the two ends of the detection coil 6 is determined in correspondence with a resistance R of the resistor and an impedance Zs of the detection coil 6. That is, $$e_0 = e \cdot Zs/(R+Zs) \qquad (1)$$

where e is the applied voltage value.

Since the detection coil 6 is wound around the ferromagnetic core 5, the voltage $e_0$ changes in proportion to the impedance Zs and the magnetic permeability of the core 5.

Figure 10:
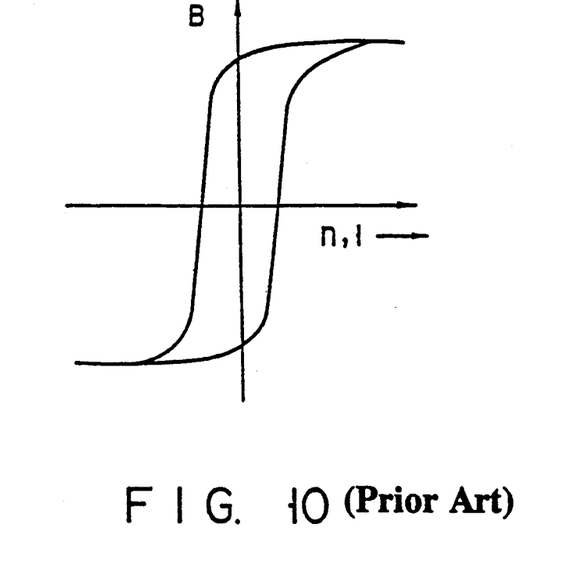
FIG. 10 is a graph showing the magnetization characteristic of a ferromagnetic core.

Assume that an AC current is supplied to the detection coil 6 while no external magnetic field is applied to the magnetic sensor 4. In this case, the magnetic permeability characteristic of the core 5 changes in accordance with the hysteresis characteristic of the core 6, as shown in FIG. 10. Note that reference symbol n denotes the number of turns of the coil; and i, a coil current.

Figure 8:
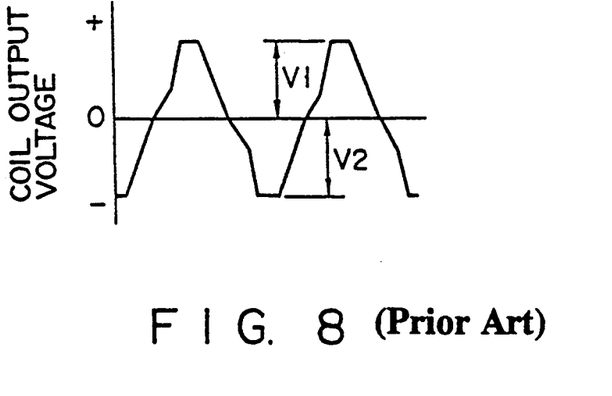
FIG. 8 is a graph showing the waveform of an output voltage from a detection coil of a magnetism detecting circuit.

For this reason, an output voltage generated across the two ends of the detection coil 6 has a waveform shown in FIG. 8. In the absence of an external magnetic field, positive and negative waveforms are symmetrical, and a positive voltage $V_1$ is equal to a negative voltage $V_2$.

Figure 9:
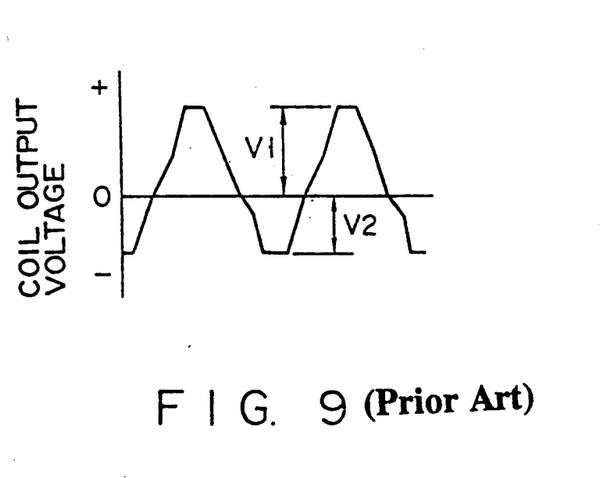
FIG. 9 is a graph showing the waveform of an output voltage from the detection coil of the magnetism detecting circuit when an external magnetic field is applied.

If an external magnetic field is applied in this state, a magnetic flux crossing the core 5 becomes a composite magnetic flux constituted by the magnetic field generated by the detection coil 6 and the external magnetic field. As a result, the waveform of a voltage generated across the two ends of the detection coil 6 exhibits $V_1 > V_2$, as shown in FIG. 9.

The external magnetic field, therefore, can be indirectly measured by obtaining the difference between the positive and negative voltages $V_1$ and $V_2$ of an output voltage generated across the two ends of the detection coil 6.

Figure 11:
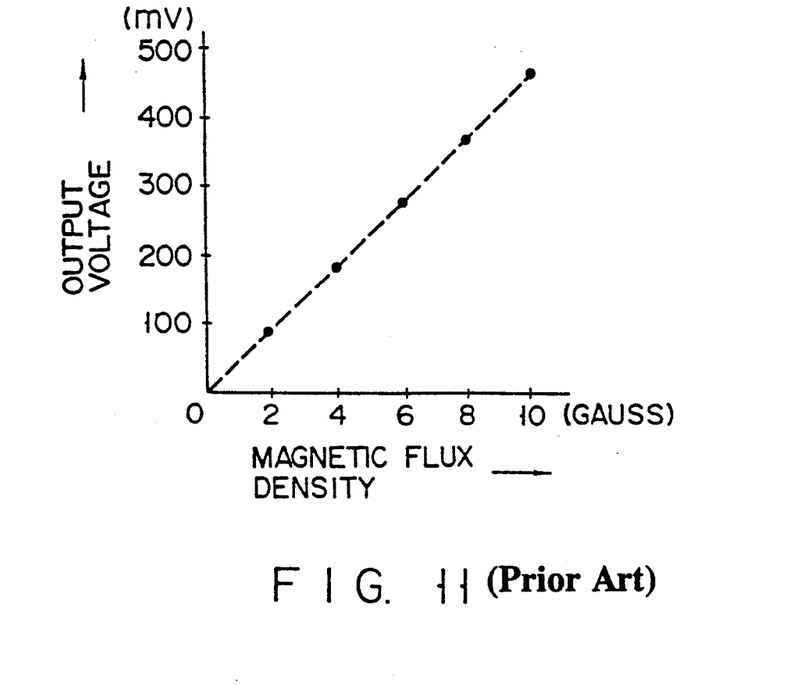
FIG. 11 is a graph showing changes in output voltage as a function of magnetic flux density in the magnetism detecting apparatus.

By using the magnetic sensor 4 of such a saturable type, output voltages $V_0$ of 0 to 500 mV can be obtained with respect to small magnetic flux densities of 0 to 10 gauss, as shown in FIG. 11.

An operation of the magnetism detecting apparatus shown in FIG. 5 will be described below with reference to the above-described operation principle and the timing chart in FIG. 6.

The rectangular signal $e_1$ output from the rectangular wave generating circuit 1 is converted into the pulse-like AC excitation signal $e_2$ by the differentiating circuit 2. The signal $e_2$ then flows in the detection coil 6 of the magnetic sensor 4 to excite the core 5. Note that the AC excitation signal $e_2$ is set to a current value at which the core 5 is magnetized up to a saturation region. In this state, therefore, the waveform of the detection signal $e_0$ indicated by the terminal voltage of the detection coil 6 exhibits a constant amplitude, as shown in FIG. 6.

In a state wherein an external magnetic field does not cross the saturated magnetic field generated by the detection coil 6, the positive and negative peak values Va and $-Vb$ of the waveform are equal to each other, as indicated by a detection signal $e_{0A}$ on the left side of FIG. 6. If, however, an external magnetic field approaches the core 5 excited to the saturation region and crosses the saturated magnetic field formed by the detection coil 6, although no change in amplitude value occurs, positive and negative peak values Va and $-Vb$ change, as indicated by a detection signal $e_{0B}$ on the right side in FIG. 6. These peak values Va and $-Vb$ are detected by the above-mentioned positive and negative detectors to be converted into a DC voltage. The above-mentioned adder adds the peak voltages $+Va$ and −Vb respectively detected by the positive and negative detectors to obtain a difference voltage (Va−Vb). The voltage detecting circuit 7 outputs this difference voltage (Va−Vb) as an output voltage $V_0$. This output voltage $V_0$ corresponds to the external magnetic field applied to the magnetic sensor 4. Therefore, a magnetic field strength can be detected by this magnetism detecting apparatus.

By using a saturable type magnetic sensor in this manner, the magnetic detection sensitivity of the apparatus can be improved, and the detection precision can be increased because a measurement result is substantially free from the influence of zero point variations due to variations in ambient temperature and the like, as compared with a magnetism detecting apparatus using a Hall element or a magnetoresistive element.

In this magnetism detecting apparatus, the ferromagnetic core 5 of the magnetic sensor 4 must be magnetized to the saturation region by supplying an AC excitation current to the detection coil 6 wound around the core 5. In order to accurately detect the positive and negative peak values Va and −Vb of the detection signal $e_0$ output from the magnetic sensor 4, a pulse signal having a trigger waveform is used as the AC excitation signal $e_2$ to be applied to the magnetic sensor 4 through the impedance element 3. Because of this trigger waveform, a high-frequency current flows in the detection coil 6. That is, in order to magnetize the core to the saturation region by using the pulse signal having the trigger waveform, an excitation current of, e.g., several 100 mA is required.

For this purpose, the voltage of the AC excitation signal $e_2$ must be greatly increased. For example, even in the compact magnetic sensor 4, the above-mentioned voltage must be 15 to 25 $V_{p-p}$. Since the rectangular wave generating circuit 1 needs to output the rectangular signal $e_1$ having a peak value of 15 to 25 $V_{p-p}$, a DC power source for applying a high voltage of 15 to 25 V is required in addition to a 5-V DC power source used in a general TTL circuit. As a result, the circuit arrangement is complicated, and the overall apparatus is increased in size. At the same time, the manufacturing cost is greatly increased.

In addition, since pulse-like noise due to pulses contained in the detection signal $e_0$ may be mixed with the output voltage $V_0$ from the voltage detecting circuit 7, a filter for removing such pulse-like noise is required.

DISCLOSURE OF INVENTION

It is an object of the present invention to realize an excitation portion and a detection portion for a magnetic sensor by a common circuit and easily saturate the core of the magnetic sensor with a small power consumption. It is a final object to simplify the circuit arrangement of a magnetism detecting apparatus, and realize a reduction in size and manufacturing cost of the overall apparatus while maintaining high measurement precision.

In order to achieve this object, according to the present invention, an oscillation current output from an oscillation circuit incorporating a detection coil of a magnetic sensor as a resonance circuit is used as a means for supplying a excitation current to the detection coil to excite the core to a saturation region.

More specifically, a magnetism detecting apparatus of the present invention uses a saturable type magnetic sensor constituted by a ferromagnetic core and a detection coil wound around the core. A parallel resonance circuit is constituted by the detection coil of the magnetic sensor and a capacitance element connected in parallel with the detection coil. In addition, an oscillation circuit incorporating the parallel resonance circuit is used. This oscillation circuit is constituted by the parallel resonance circuit and an amplifier to which the parallel resonance circuit and a resistor are connected as a feedback circuit. With this arrangement, the oscillation circuit oscillates at the resonance frequency of the parallel resonance circuit. Furthermore, an AC oscillation current having the resonance frequency flows in the detection coil constituting the parallel resonance circuit. In this case, the current value of the oscillation current flowing in the detection coil is set to excite the ferromagnetic core to the saturation region. The apparatus further includes a waveform change detecting circuit for detecting a change in waveform of an output signal from the oscillation circuit.

While no external magnetic field is applied to the magnetic sensor, the amplitude of an output signal from the parallel resonance circuit, indicated by the terminal voltage of the detection coil, is constant because the core is excited to the saturation region. Note that the output signal from the oscillation circuit is amplified to positive and negative saturation voltage levels with respect to a reference level, e.g., 0 V, and is stabilized by an amplifier having a positive feedback circuit.

When an external magnetic field crosses the magnetic sensor in this state, the external magnetic field is added to or subtracted from an AC magnetic field produced by the core which has been excited to the saturation region by the detection coil. As described above, the voltage level across the two ends of the detection coil, i.e., the voltage level of the output signal from the parallel resonance circuit, changes in the positive or negative direction which is determined by the direction of the external magnetic field. As a result, the signal level of the output signal from the oscillation circuit also changes in the positive or negative direction. As described above, since the output signal is amplified to the positive and negative saturation voltage levels and is stabilized by the amplifier, the positive- and negative-side waveforms become asymmetric.

Therefore, by detecting the amount of change in waveform of this output signal using the waveform change detecting circuit, the external magnetic field can be indirectly detected As described above, an external magnetic field can be accurately measured by using only the oscillation circuit incorporating the detection coil as part of the positive feedback circuit, and the waveform change detection circuit.

BEST MODE OF CARRYING OUT THE INVENTION

An embodiment of the present invention will be described below with reference to the accompanying drawings.

Figure 1:
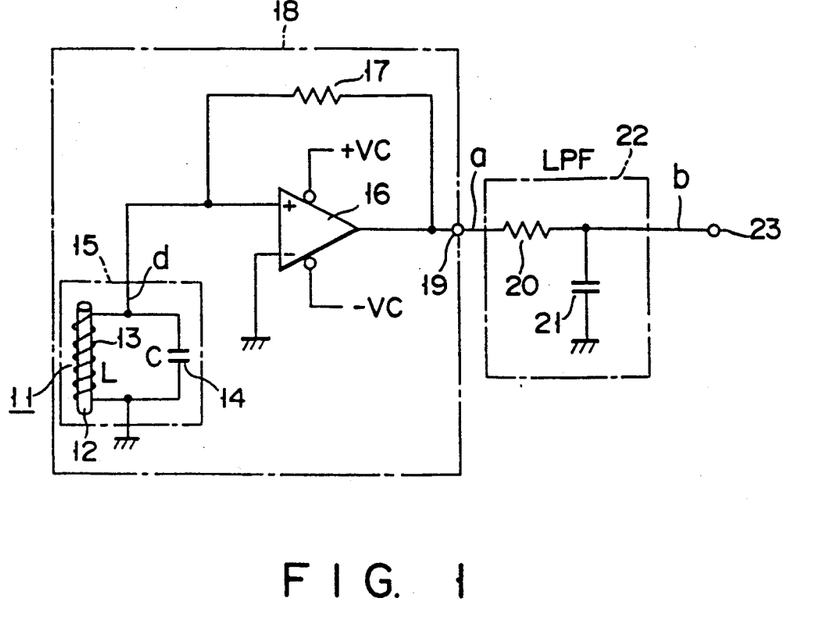
FIG. 1 is a block diagram showing a schematic arrangement of a magnetism detecting apparatus according to an embodiment of the present invention.

FIG. 1 is a block diagram showing a schematic arrangement of a magnetism detecting apparatus according to an embodiment.

A magnetic sensor 11 comprises a core 12 constituted by, e.g., a rod-like ferromagnetic member, and a detection coil 13 wound around the core 12, as shown in FIG. 1. A capacitor 14 is connected in parallel with the detection coil 13 of the magnetic sensor 11. The detection coil 13 and the capacitor 14 constitute a parallel resonance circuit 15. One end of the parallel resonance circuit 15 is grounded, while the other end is connected to the noninverting (+) input terminal of a differential amplifier 16. The inverting (−) input terminal of the differential amplifier 16 is grounded. A feedback resistor 17 is connected between the output terminal and noninverting input terminal of the differential amplifier 16.

The differential amplifier 16 is a so-called twopower source type amplifier, which is started when DC source voltages $+V_C$ and $-V_C$ are externally applied. The differential amplifier 16 then amplifies a signal, input to the noninverting input terminal, equally to the positive and negative sides, with reference to a ground voltage (0 V) as a reference voltage level. In such a circuit, the feedback resistor 17 and the parallel resonance circuit 15 constitute a positive feedback circuit with respect to the differential amplifier 16. As a result, the parallel resonance circuit 15, the feedback resistor 17, and the differential amplifier 16 constitute a kind of an oscillation circuit 18.

As is known, the oscillation frequency of the oscillation circuit 18 is a resonance frequency $f_0$ determined by equation (1) based on an inductance L of the detection coil 13 and a capacitance C of a capacitor 14 of the parallel resonance circuit 15.

$$f_0 = 1/(2\pi\sqrt{LC}) \quad (2)$$

Note that in the apparatus of this embodiment, a number N of turns of the detection coil 13 is 100, the inductance L is about 2.16 mH, and the capacitance C of the capacitor 14 is about 3,000 pF. Therefore, the resonance frequency $f_0$ is about 62.5 kHz.

The resonance circuit 18 outputs an output signal having the frequency $f_0$ from an output terminal 19. In addition, an excitation current having the resonance frequency $f_0$ flows in the detection coil 13 of the parallel resonance circuit 15 incorporated in the resonance circuit 18. This excitation current then excites the core 12 of the magnetic sensor 11. The value of this excitation current is set such that the core 12 is excited to the saturation region. More specifically, the current value is set by adjusting the circuit constant of the respective electronic circuits constituting the resonance circuit 18. Therefore, the core 12 is excited to the saturation region all the time.

An output signal a output from the output terminal 19 of the oscillation circuit 18 is input to a low-pass filter (to be referred to as an LPF hereinafter) 22 as a waveform change detecting circuit constituted by a resistor 20 and a capacitor 21. This LPF 22 has a large time constant and serves to detect only the DC components of the output signal a input thereto. An output signal from the LPF 22 is output, as a waveform change amount signal b, to an output terminal 23.

An operation of the magnetism detecting apparatus having the above-described arrangement will be described below with reference to the timing chart in FIG. 3.

When the power source of the magnetism detecting apparatus is turned on at time $t_0$ while an external magnetic field H is not close to the magnetic sensor 11, the source voltages $+V_C$ and $-V_C$ are applied from a power source circuit (not shown) to the differential amplifier 16. The differential amplifier 16 is then started. Since the feedback resistor 17 and the parallel resonance circuit 15 constitute a positive feedback circuit, as described above, the oscillation circuit 18 starts an oscillating operation. As a result, an oscillation current flows in the detection coil 13 as one component of the parallel resonance circuit 15. This oscillation current serves as an excitation current to excite the core 12 of the magnetic sensor 11 to the saturation region. A terminal voltage d (output signal) of the parallel resonance circuit 15 and the output signal a from the output terminal 19 become periodic waves, each having the resonance frequency $f_0$ (period T), as shown in FIG. 3.

In this case, the amplification factor of the differential amplifier 16 is set to be large. Therefore, the differential amplifier 16 amplifies the terminal voltage d of the parallel resonance circuit 15 to positive and negative saturation voltage levels, with reference to 0 V applied to the inverting input terminal as a reference voltage, and is set in a stable state. Consequently, as shown in FIG. 3, the output signal a from the oscillation circuit 18 has a rectangular waveform exhibiting that the upper and lower portions of each sine waveform are flat, and the positive and negative peak values are equal to each other and constant. Therefore, a pulse width $T_A$ of the positive waveform of the output signal a having a period T is equal to a pulse width $T_B$ of the negative waveform ($T_A = T_B$). This output signal a is converted into a DC signal by the LPF 22 having a large time constant, and is output, as the waveform change amount signal b, to the output terminal 23. In this case, since the pulse width $T_A$ of the positive waveform is equal to the pulse width $T_B$ of the negative waveform, the waveform change amount signal b is 0 V.

Figure 3:
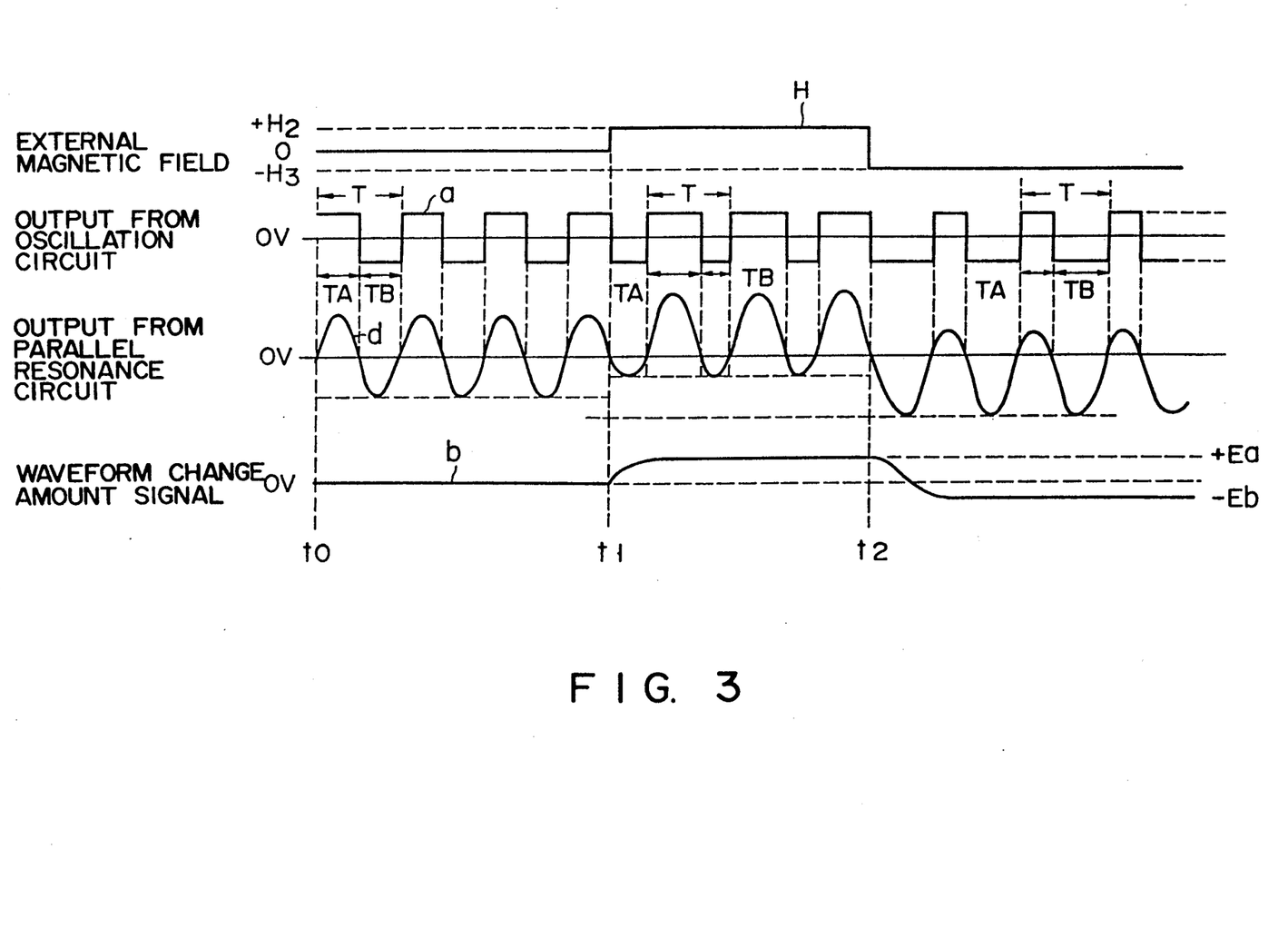
FIG. 3 is a timing chart showing an operation of the apparatus of the embodiment.

In this state, if an external DC magnetic field $+H_2$ crosses the saturated core 12 of the magnetic sensor 11 at time $t_1$, although the terminal voltage (output signal) of the magnetic sensor 11, i.e., the amplitude value of the terminal voltage d of the parallel resonance circuit 15, does not change, the overall signal level is shifted to, e.g., the positive side, as shown in FIG. 3. As a result, although the positive and negative peak values of the output signal a from the oscillation circuit 18 do not change, the positive portion of the waveform of the terminal voltage d applied to the noninverting input terminal of the differential amplifier 16 becomes larger than the negative portion of the waveform. Therefore, the pulse width $T_A$ of the positive waveform becomes larger than the pulse width $T_B$ of the negative waveform ($T_A > T_B$). As a result, the waveform change amount signal b output from the LPF 22 changes from 0 V to $+Ea$. This voltage ($+Ea$) corresponds to the external magnetic field $H_2$.

If an external magnetic field $-H_3$ having a polarity opposite to the external magnetic field $H_2$ crosses the saturated core 12 of the magnetic sensor 11 at time $t_2$, the signal level of the terminal voltage d of the magnetic sensor 11 is shifted to the negative side, as shown in FIG. 3. Since the positive portion of the waveform of the terminal voltage d applied to the noninverting input terminal of the differential amplifier 16 becomes smaller than the negative portion of the waveform, the pulse width $T_A$ of the positive waveform of the output signal a from the oscillation circuit 18 becomes smaller than the pulse width $T_B$ ($T_A < T_B$). As a result, the waveform change amount signal b output from the LPF 22 changes to $-Eb$. This voltage value ($-Eb$) corresponds to the external magnetic field $-H_3$.

In this manner, the external magnetic field H crossing the core 12 of the magnetic sensor 11 can be indirectly measured as the voltage value of the waveform change amount signal b.

Figure 2:
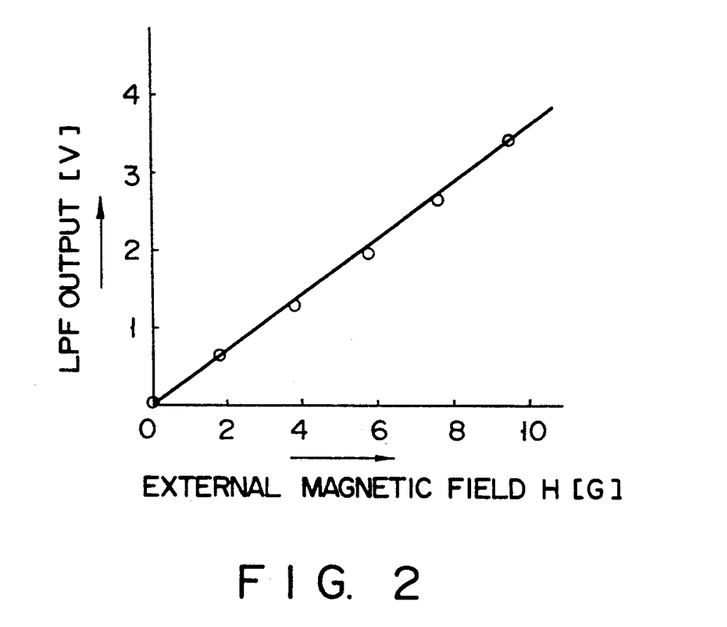
FIG. 2 is a graph showing the relationship between the external magnetic field and the output voltage in the apparatus of the embodiment.

FIG. 2 is a graph showing the relationship between the external magnetic field H (gauss) accurately measured in advance by another reference magnetism measuring apparatus and the voltage of the waveform change amount signal b output from the output terminal 23 of the apparatus of this embodiment. As shown in FIG. 2, it is confirmed that an accurate output characteristic proportional to the external magnetic field H can be obtained. In addition, a relatively large output voltage of several volts can be obtained with respect to the external magnetic field H.

In the magnetism detecting apparatus having the above-described arrangement, as shown in FIG. 1, the oscillation circuit 18 constituted by the differential amplifier 16 and a pair of inexpensive electronic elements, i.e., the feedback resistor 17 and the capacitor 14, can serve both as an excitation portion and a detection portion with resect to the magnetic sensor 11. Therefore, the circuit arrangement can be greatly simplified as compared with the conventional magnetism detecting apparatus which requires the rectangular wave generating circuit 1, the differentiating circuit 2, the voltage detecting circuit 7, and the like, shown in FIG. 5. Consequently, the overall magnetism detecting apparatus can be reduced in size and weight. In addition, the manufacturing cost of the magnetism detecting apparatus can be greatly decreased.

The AC excitation current which is applied to the detection coil 13 to excite the core 12 of the magnetic sensor 11 to the saturation region is an oscillation current having a sine waveform output from the oscillation circuit 18. It is relatively easy to increase the value of this oscillation current. In addition, the oscillation current need not have a pulse waveform, unlike the conventional apparatus. Therefore, the load current of the differential amplifier 16 is reduced, and so is the power consumption of the differential amplifier 16.

In addition, as shown in FIG. 2, since high detection sensitivity can be obtained with respect to a small external magnetic field H, the waveform change amount signal b output from the LPF 22 need not be amplified by using another amplifier.

In addition, if the correspondence values between the external magnetic field H and the output voltage b are measured as calibration values in advance, as shown in FIG. 2, measurement with respect to unknown magnetic fields can be easily performed without adjustments.

Furthermore, in a conventional magnetism detecting apparatus using a simple pickup coil based on the electromagnetic induction effect or the like, only a magnetic field which changes over time can be measured because of its measurement principle. However, in the magnetism detecting apparatus of the present invention, since the magnetic sensor 11 which is excited to the saturation region in advance is used, magnetic fields can be accurately measured throughout a wide frequency range from DC magnetic fields to high-frequency magnetic fields.

Moreover, according to the present invention, the amount of change in waveform of the output signal a from the oscillation circuit 18 due to the external magnetic field H is measured, and the strength of the external magnetic field is detected on the basis of the change amount. Since a waveform itself is not easily influenced by external environmental conditions such as temperature, no special temperature compensation measures need be provided for the oscillation circuit 18.

The present invention is not limited to the embodiment described above. In the above embodiment, the DC external magnetic fields $+H_2$ and $-H_3$ respectively having S and N poles are measured. As described above, however, AC external magnetic fields can also be measured.

Figure 4:
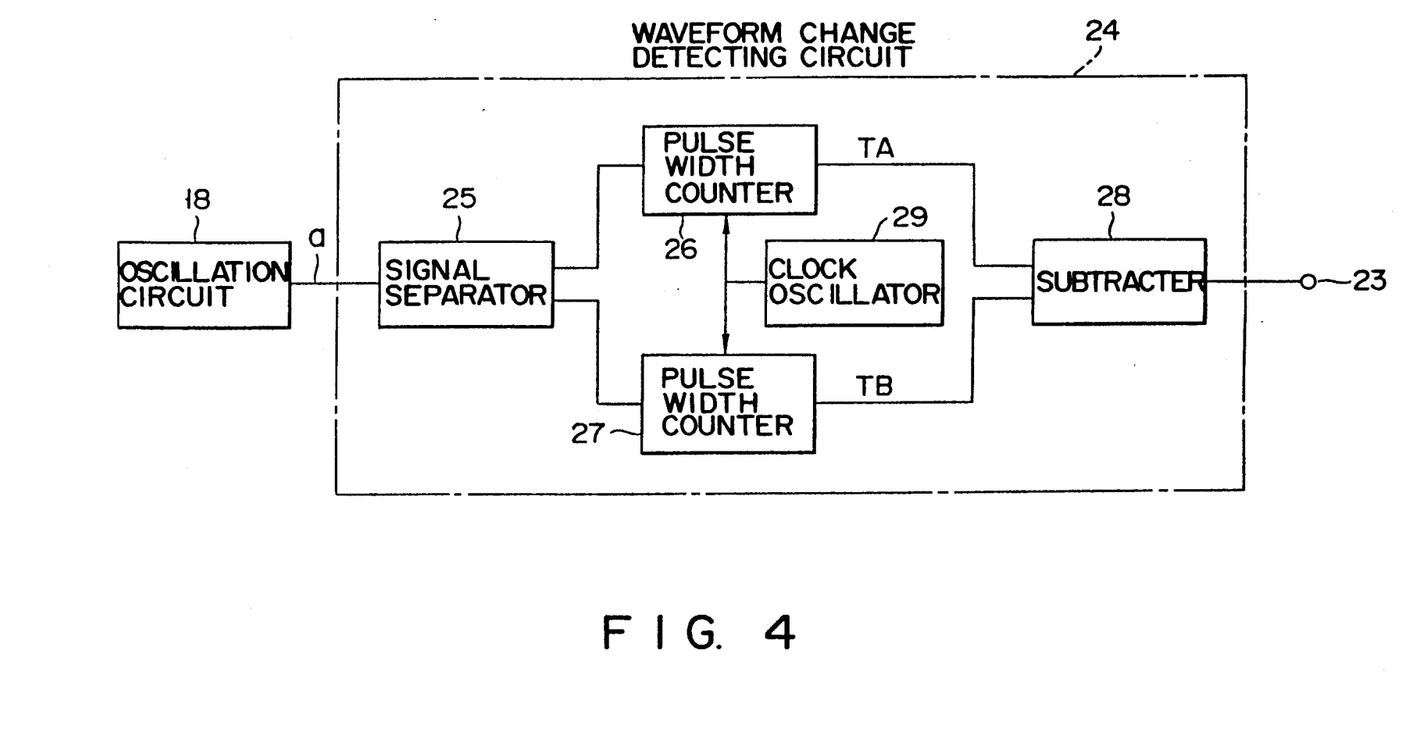
FIG. 4 is a block diagram showing a schematic arrangement of a waveform change detecting circuit in a magnetism detecting apparatus according to another embodiment of the present invention.

FIG. 4 is a block diagram showing a schematic arrangement of a magnetism detecting apparatus according to another embodiment of the present invention. The same reference numerals in FIG. 4 denote the same parts as in FIG. 1, and a repetitive description will be avoided.

In the magnetism detecting apparatus of this embodiment, a waveform change detecting circuit 24 comprises a signal separator 25, a pulse width counter 26 as a positive-side pulse width measuring circuit, a pulse width counter 27 as a negative-side pulse width measuring circuit, a subtracter 28, and a clock oscillator 29.

An output signal a having the rectangular waveform shown in FIG. 3, output from an oscillation circuit 18, is input to the signal separator 25. The signal separator 25 separates the output signal a into positive and negative waveform components with the 0 volt line serving as a boundary. The separated positive and negative waveform components are respectively input to the pulse width counters 26 and 27.

The pulse width counter 26 starts counting the clocks of clock signal output from the clock oscillator 29 in synchronism with the leading edge of the pulse waveform of the input positive waveform component, and stops the counting operation in synchronism with the trailing edge of the pulse waveform of the positive waveform component. With this operation, the pulse width counter 26 measures a pulse width $T_A$ of the positive waveform component. On the other hand, the pulse width counter 27 starts counting the clocks of a clock signal output from the clock oscillator 29 in synchronism with the trailing edge of the pulse waveform of the input negative waveform component, and stops the counting operation in synchronism with the leading edge of the pulse waveform of the negative waveform component. With this operation, the pulse width counter 27 measures a pulse width $T_B$ of the negative waveform component.

The pulse width counters 26 and 27 respectively supply the data of the measured pulse widths $T_A$ and $T_B$ to the subtracter 28. The subtracter 28 calculates a difference $(T_A - T_B)$ between the input pulse widths $T_A$ and $T_B$ and outputs the difference $(T_A - T_B)$ as a digital waveform change amount signal. Therefore, the difference $(T_A - T_B)$ corresponds to an external magnetic field H.

As described above, since an external magnetic field can be obtained as a digital value, the obtained external magnetic field H can be directly input to an external unit such as a computer.

We claim:

1. A device for sensing magnetism, comprising:
   a magnetic sensor having a ferromagnetic core and a detection coil wound around said core;
   a parallel resonance circuit comprising said detection coil of said magnetic sensor, and a capacitance element connected in parallel with said detection coil, said parallel resonance circuit providing an output signal;
   a DC level of said output signal of said parallel resonance circuit changing in accordance with a change in an external magnetic field without changing a waveform of said output signal of said parallel resonance circuit;
   an oscillation circuit including:
      an amplifier having an output and an input; and
      a feedback circuit comprising said parallel resonance circuit and a resistor coupled between said output and said input of said amplifier; and
   a waveform change detecting circuit for detecting a change in a waveform of an output signal from said oscillation circuit, said waveform change detecting circuit comprising:
      a signal separator for separating said output signal of said oscillation circuit into a first positive waveform component and a second negative waveform component;
      a positive pulse width measuring circuit for measuring a width of said first positive waveform component separated by said signal separator;
      a negative pulse width measuring circuit for measuring a width of said second negative wavefrom component separated by said signal separator; and
      subtracting circuit means for subtracting a first pulse width measured by one of said positive and negative pulse width measuring circuits from a second pulse width measured by the other one of said positive and negative pulse width measuring circuits.

2. A device for sensing magnetism, comprising:
   a magnetic sensor having a ferromagnetic core and a detection coil wound around said core;
   a parallel resonance circuit comprising said detection coil of said magnetic sensor, and a capacitance element connected in parallel with said detection coil, said parallel resonance circuit providing an output signal;
   a DC level of said output signal of said parallel resonance circuit changing in accordance with a change in an external magnetic field without changing a waveform of said output signal of said parallel resonance circuit;
   an oscillation circuit including:
      a differential amplifier having an output terminal and first and second input terminals, said first input terminal being connected to a ground potential, and said second input terminal being connected to receive said output signal from said parallel resonance circuit so that said differential amplifier amplifies said output signal from said parallel resonance circuit into positive and negative portions when measured with respect to said ground potential;
      a feedback circuit, comprising said parallel resonance circuit and a resistor, said resistor being coupled between said output terminal and said second input terminal of said differential amplifier;
   said parallel resonance circuit being connected between an input terminal of said resistor and said ground potential; and
   a waveform change detecting circuit for detecting a change in a waveform of an output signal from said oscillation circuit,
   said waveform change detecting circuit comprising:
      a signal separator for separating said output signal of said oscillation circuit into a first positive waveform component and a second negative waveform component;
      a positive pulse width measuring circuit for measuring a width of said first positive waveform component separated by said signal separator;
      a negative pulse width measuring circuit for measuring a width of said second negative wavefrom component separated by said signal separator; and
      subtracting circuit means for subtracting a first pulse width measured by one of said positive and negative pulse width measuring circuits from a second pulse width measured by the other one of said positive and negative pulse width measuring circuits.

3. The device for sensing magnetism according to claim 1, wherein said positive pulse width measuring circuits respectively comprise pulse width counters.

4. The device for sensing magnetism according to claim 2, wherein said positive and negative pulse width measuring circuit respectively comprise pulse width counters.

* * * * *